United States Patent [19]

Folestad et al.

[11] Patent Number: 6,162,465
[45] Date of Patent: Dec. 19, 2000

[54] METHOD AND AN INDUSTRIAL PROCESS FOR DETERMINING DOSE-LEVEL CHARACTERISTICS OF A MULTIPLE UNIT SYSTEM

[75] Inventors: Staffan Folestad; Johan Gottfries; Arne Torstensson, all of Mölndal; Gunnar Zackrisson; Göran Östling, both of Södertälje, all of Sweden

[73] Assignee: Astra Aktiebolag, Sodertalje, Sweden

[21] Appl. No.: 09/101,114

[22] PCT Filed: Jun. 8, 1998

[86] PCT No.: PCT/SE96/01094

§ 371 Date: Jun. 30, 1998

§ 102(e) Date: Jun. 30, 1998

[87] PCT Pub. No.: WO98/58254

PCT Pub. Date: Dec. 23, 1998

[30] Foreign Application Priority Data

Jun. 18, 1997 [SE] Sweden ................................... 9702338

[51] Int. Cl.⁷ .............................. A61K 9/20; A61K 9/26; A61K 9/54; A61K 9/58
[52] U.S. Cl. .......................... 424/458; 424/451; 424/462; 424/464; 424/469; 424/470; 424/489; 424/490; 424/497
[58] Field of Search ..................................... 424/451, 464, 424/489, 490, 458, 462, 469, 470, 497

[56] References Cited

U.S. PATENT DOCUMENTS

| | | | |
|---|---|---|---|
| 4,472,960 | 9/1984 | Motoyama et al. | 73/7 |
| 4,772,475 | 9/1988 | Fukui et al. | 424/468 |
| 4,927,640 | 5/1990 | Dahlinder et al. | 424/497 |
| 4,957,745 | 9/1990 | Jonsson | 424/461 |
| 4,994,260 | 2/1991 | Källstrand et al. | 424/10 |
| 5,085,868 | 2/1992 | Mattsson et al. | 424/490 |
| 5,688,519 | 11/1997 | Leonard | 424/426 |

FOREIGN PATENT DOCUMENTS 4101677 7/1992 Germany.

OTHER PUBLICATIONS

Sandberg et al. Steady–state bioavailability and day–to–day variability of a multiple unit (CR/ZOK) on a single unit (OROS) delivery system of metoprolol after once–daily dosing. Pharm. Res. 10(1): 28–34, 1993.

*Primary Examiner*—James M. Spear
*Attorney, Agent, or Firm*—White & Case LLP

[57] ABSTRACT

The invention relates to a method for the determination of dose-level characteristics, such as physicochemical properties, functionality and/or quality, of a multiple unit system comprising a plurality of individual subunits (12). A number of said subunits (12) are individually analysed for obtaining precise characteristics for each individually analysed subunit (12). Said dose-level characteristics of the multiple unit system are determined based the thus-obtained precise characteristics for each individually analysed subunit (12). The invention also relates to an industrial process in which this method is used, and to the use of the claimed method in a process for designing a multiple unit system formulation product.

22 Claims, 4 Drawing Sheets

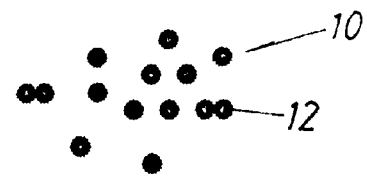
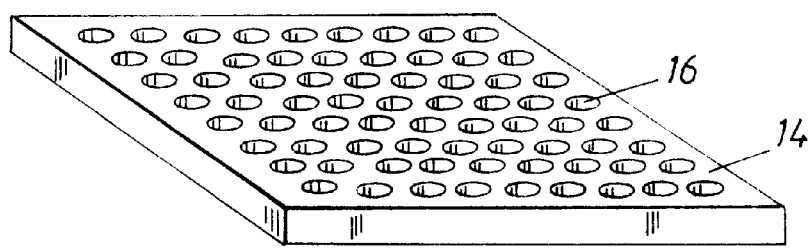
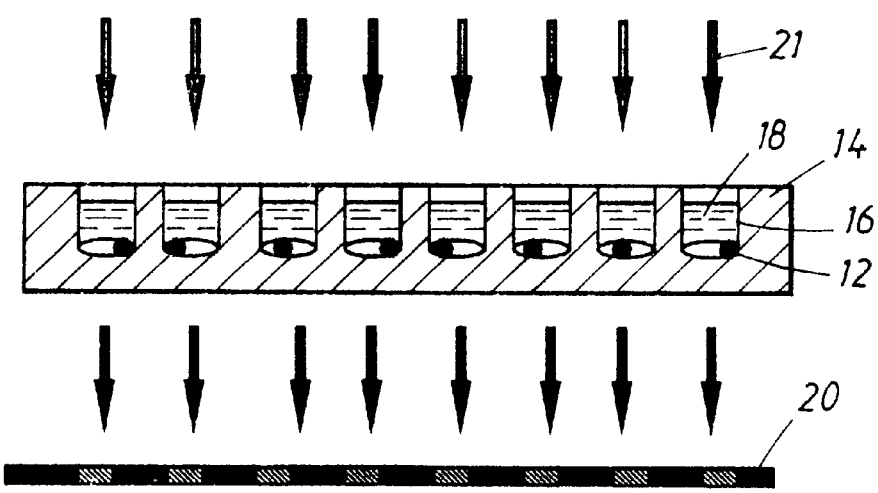

METHOD AND AN INDUSTRIAL PROCESS FOR DETERMINING DOSE-LEVEL CHARACTERISTICS OF A MULTIPLE UNIT SYSTEM

This application is a 371 of PCT/SE96/01094 filed Jun. 8, 1998.

FIELD OF THE INVENTION

The present invention broadly relates to the field of so called multiple unit systems, especially but not exclusively pharmaceutical formulations designed as multiple unit dosage forms. More specifically, the invention relates to a method for determining characteristics on dose-level of multiple unit systems, such as dose-level properties relating to the release rate or release profile of one or more active substances. Other aspects of the invention relates to an industrial process for the manufacture of multiple unit system formulations, including such a method, and to the use of the method in a process for designing a multiple unit system formulation product.

The present invention is especially useful in connection with in vitro dissolution tests on drug products where the therapeutic performance of drugs is highly dependent on the drug dissolution properties. Therefore, the technical background of the invention and objects and embodiments thereof, will be described with reference to such dissolution tests. However, the invention may also be applicable in connection with tests on other industrial products than pharmaceutical drugs, such as food industry products. The invention may also be implemented by the use of non-destructive tests.

BACKGROUND

Pharmaceutical formulations can be designed as Multiple Unit Systems, an example of which is the so called MUPS (Multiple Unit Pellet Systems), where a dose is administrated for example as a tablet (tableted dosage form) or as a capsule (capsulated dosage form), each dose comprising a plurality of individual pellets or granules, referred to as subunits in the following. Each subunit carries one or more active drug or substance. A typical number of subunits in one dose form is 50, 100, 1000 or more.

Prior art discloses many different types of units intended for MUPS, such as for instance those described in U.S. Pat. No. 5,085,868. Usually, this type of formulation is preferred for controlled or sustained release formulations as well as for enteric coated formulations. The dose of the active substance may be administrated in the form of a tablet or a capsule or a like which disintegrates to make available a multitude of coated subunits, which release the active substance during the dissolution. Other prior-art MUPS are disclosed in U.S. Pat. No. 4,957,745, U.S. Pat. No. 4,927,640, U.S. Pat. No. 4,994,260, and U.S. Pat. No. 5,085,868.

Today, the common test procedure for determining the content, the functionality and/or the quality, etc. of MUPS is to analyze the formulation on a dose-level, i.e. to perform the analysis on a whole tablet or capsule. In conventional methods for determining the dose-level release profile the dosage form is placed in a test solution (in vitro testing) under controlled conditions, whereupon the test solution containing the dissolved active substance is analysed, typically by determining a release profile by the use of an optical absorption measurement.

However, MUPS are characterised in that the dose is the summation of the individual subunits and, therefore, by such prior-art test methods for analysing properties on dose-level of MUPS one only obtains a measurement of the cumulative release property of the entire subunit population. Variations in structure and release property between the individual subunits are not detectable, such as variations in film thickness, film defects, uneven subunit surfaces, deviations from spherical form of some subunits, etc. As a result, with presently available MUPS test methods it is not possible to identify the exact causes leading to unintended or intended variations on dose-level, such as variations in the release profile. Thus, even if it is possible to identify an "error" in the test results obtained by the conventional dose-level test methods, these methods will limit the possibilities to measure the product quality in terms of process parameters, i.e. the possibility to achieve detailed information is limited.

Dissolution testing provides essential information for the development of formulations, but the above limitations of the conventional test methods creates undesired limitations for obtaining a desired release profile. Especially, these limitations make it difficult to obtain a sufficiently exact and reproducible release profile.

Many mathematical models have been suggested in the literature for the description of release profiles. These models suffer from the drawback that it is difficult to correlate the obtained data, completely or partly, with a model when the result can be due to unknown sample variations.

SUMMARY OF THE INVENTION

The present invention is based on the insight that the functionality and quality of an entire dose or a MUPS dosage is directly correlated to the functionality and quality of the individual subunits forming said dose. One example thereof is film-coated pellets where the individual pellets are designed to deliver the active drug(s) at a specified and controlled rate. Another example of such functionality of a pellet film is to protect the pellets from deterioration during the administration (enteric coating).

The present invention is also based on the insight that further information is required in order to make it possible to optimize process parameters in the manufacturing of products having a multiple unit systems design.

In one aspect of the invention, there is provided a method for the determination of dose-level characteristics, such as physicochemical properties, functionality and/or quality, of a multiple unit system comprising a plurality of individual subunits, characterised by the step of individually analyzing a number of said subunits (subunit-level) for obtaining precise characteristics for each individually analyzed subunit, and the step of determining said dose-level characteristics of the multiple unit system based the thus-obtained precise characteristics for each individually analyzed subunit.

The method according to the invention will increase the possibilities for obtaining essential information from which new pharmaceutical multiple unit system formulations can be developed or designed. Also, the invention will be useful in connection with determining characteristics of existing multiple unit system products, such as the homogeneity, the distribution profile of the film thickness, etc. Furthermore, the manufacture of multiple unit systems may be optimized in detail for obtaining higher product qualities, e.g. by the development of better theoretical models describing how the characteristics on subunit-level influence on the dose-level characteristics, e.g. how the properties of the individual subunits influence on a dose-level release profile.

The multiple unit system may be a pharmaceutical multiple unit dosage formulation, such as a tablet or a capsule, and the subunits may comprise at least one active drug. Said subunits may comprise a protective film, such as a film giving a controlled release of an active drug, or an enteric coating polymer.

The number of subunits which are individually analyzed is preferably determined with respect to the number of subunits included in the multiple unit system, and an statistical accuracy to be obtained in the determination of said dose-level characteristics. Specifically, the number of subunits which are individually analyzed may be equal to, or essentially equal to, the number of subunits included in the multiple unit system. In general, the number of subunits to be individually analyzed will have to be so high that the features or characteristics of the entire dose can be predicted, evaluated or determined with an accuracy which is acceptable under the actual circumstances.

The step of individually analyzing the subunits may comprise the step of performing a destructive test on each analyzed subunit, especially a dissolution test for individual monitoring the dissolution characteristics of film-coated subunits.

The individual analysis on the subunits may be performed in parallel, e.g. by using a micro-titer equipment with a plate containing a plurality of wells, where one subunit is placed in each well. The release of the drug(s) in a liquid, such as a buffer system, can then be monitored by different techniques, such as absorption spectrometry (e.g. UV-VIS, NIR, IR), emission spectrometry (e.g. fluorescence), scattering spectrometry (e.g. Raman) and electrochemical techniques (e.g. amperometry, coulometry, conductometry). Alternative procedures can also be based on the use of techniques where a small portion of the dissolution media is frequently sampled from each respective well by using single- or multiple-capillary systems, whereafter the samples are subjected to e.g. flow-injection analysis or any separation technique (e.g. capillary electrophoresis, liquid chromatography).

In accordance with the invention, the step of individually analyzing the subunits may include not only destructive tests, such as a dissolution test, but also non-destructive tests, using e.g. NIR spectrometry or other detection techniques (e.g. Raman, fluorescence, X-ray). The information in a NIR spectrum is correlated to the release profile and can be determined within a very short time, such as 10 ms. One possible solution would be to focus the NIR beam down on the individual subunits by using fiber optics, a microscope or the equivalent. Subunits with damaged films or variations in film thickness can be identified in the NIR spectra obtained or by other techniques.

In one aspect of the invention, there is also provided an industrial process for the manufacture of multiple unit system formulations, including a method according to the invention, wherein the obtained precise characteristics for each individually analyzed subunit are continuously used in the process as feed-back control data in the process in order to maintain predetermined dose-level characteristics of the manufactured multiple unit system formulations. The invention also encompasses the use of the inventive method in a process for designing a multiple unit system formulation product.

The above and other features of the invention are set out in the claims.

BRIEF DESCRIPTION OF THE DRAWINGS

FIG. 1 is a schematic representation of a micro-titer tray and a sample of subunits, for performing a subunit dissolution test in accordance with an embodiment of the invention.

FIG. 2 illustrates the use of the micro-titer tray in FIG. 1.

DETAILED DESCRIPTION OF THE INVENTION

Figure 3:
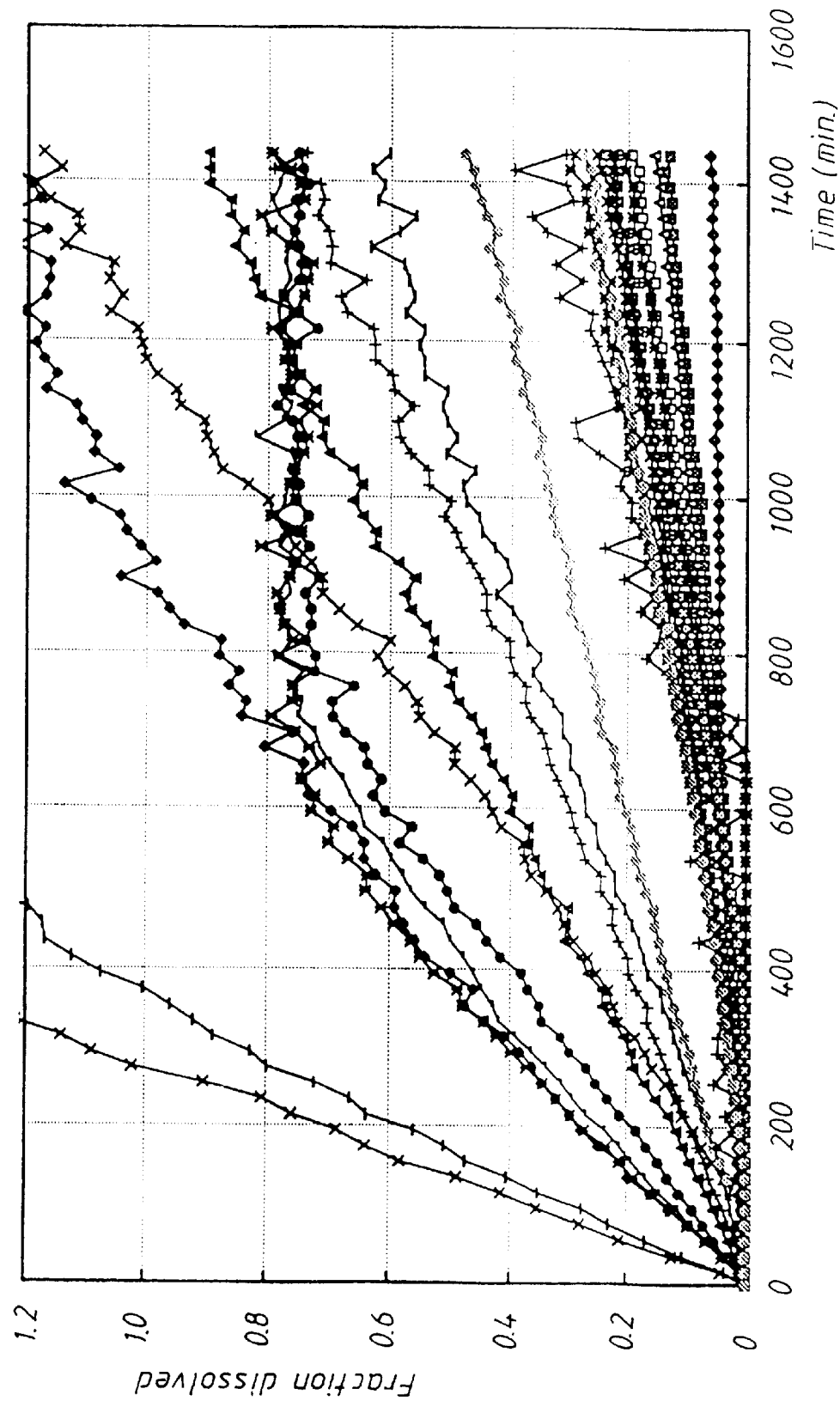
FIG. 3 shows dissolution profiles from a plurality of subunits.
Figure 4:
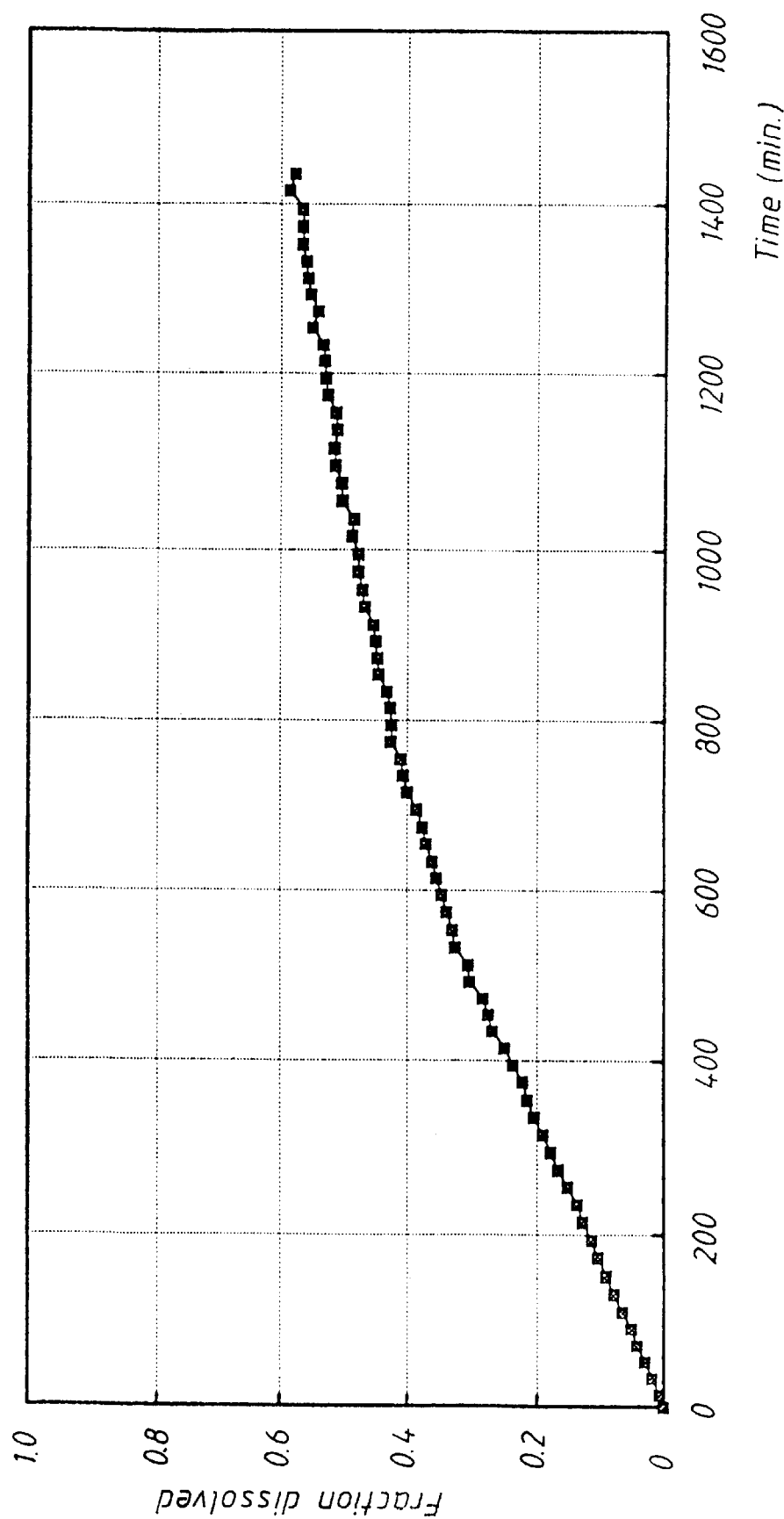
FIG. 4 shows a mean dissolution profile from a plurality of subunits.

The applicant has performed experiments according to the inventive method, using an analyse equipment having a large number of separate wells (96 or 384 well plates (ELISA)) for the dissolution, and a Spectra MAX spectrophotometer (wavelength 250 nm–750 nm) for performing an individually detection of dissolved substance in each well.

FIG. 1 illustrates a sample 10 of subunits 12, and a sample tray 14 having a plurality of separate wells 16. As illustrated in FIG. 2, during the measurement each well 16 contains one subunit 12 and a predetermined volume of a test solution 18. The total dissolution volume 18 in each well 16 was 300 $\mu$L. A multichannel detector 20 receives light or radiation 21 passing through each well 16. Alternative optical designs can be used, such as confocal coupling of light and detection.

In order to avoid interference between the subunits 12 present in each well 16 and the optical path of the spectrophotometer, the microplate 14 may be tilted and/or shaken during the analysis. Such interference can also be avoided by stirring the contents of each well, e.g. by the use of a small glass bead in each one of the wells 16.

The active substance in the subunits 12 was remoxipride in the form of subunits (microcapsules). Remoxipride microcapsules for control release capsules (Ethanol based coating on microcapsules) are manufactured by coating remoxipride microcapsules in a fluidized bed. Uncoated microcapsules are charged and a polymer solution is sprayed onto the microcapsules. The microcapsules are then dried in the fluidized bed and emptied from the bed. The thus-prepared microcapsules are aerated to remove solvent residues. Finally, the microcapsules are passed through a screen to remove agglomerates and fines.

The experiments illustrate that there is a large variation in the dissolution profiles of the individual subunits, see FIG. 3. With an analysis on the subunit-level, the release profile of each individual subunit or pellet presents an initial lagtime-phase and a subsequent steady-state phase. Contrary to the essentially linear appearance of the release profile on subunit-level, a dissolution test on dose level (the entire dose) results in an essentially different release profile.

Figure 5:
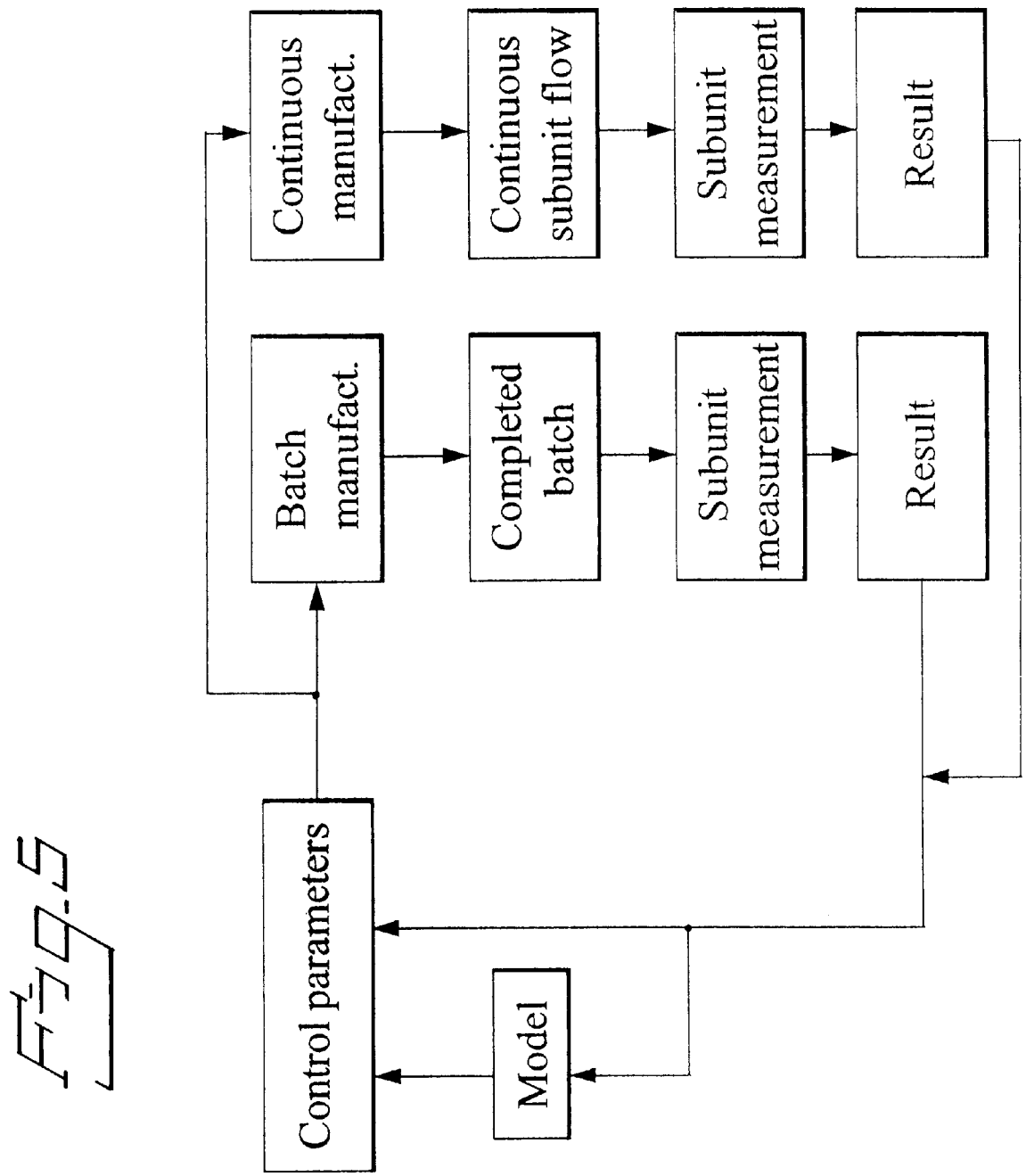
FIG. 5 illustrates an implementation of the invention in an industrial process.

FIG. 5 is a schematic diagram illustrating how the invention may be implemented in an industrial process for the manufacture of multiple unit system formulations. The subunit measurement may be performed on subunits in a completed batch, or on subunits in a continuous subunit flow. In either case, the obtained precise characteristics for each individually analysed subunit may be used as feed-back control data for the calculation of process parameters, in order to obtain predetermined dose-level characteristics of the manufactured multiple unit system formulations. Optionally, a process model can be used for receiving the control data in order to calculate the process parameters.

What is claimed is:

1. A method for determining physiochemical dose-level characteristics of a pharmaceutical unit dose of a multiple unit system comprising a plurality of individual subunits (12), the method comprising the step of individually analyzing a number of said subunits (12) to obtain precise characteristics for each individually analyzed subunit (12), and the step of determining said dose-level characteristics of the multiple unit system based on the thus-obtained precise characteristics for each individually analyzed subunit (12).

2. The method according to claim 1, wherein the pharmaceutical multiple unit dosage formulation is a tablet, a capsule, or any other unit dose comprising a plurality of subunits.

3. The method according to claim 1, wherein the number of subunits (12) which are individually analyzed is determined with respect to the number of subunits (12) included in the multiple unit system, and a statistical accuracy in the determination of said dose-level characteristics.

4. The method according to claim 3, wherein the number of subunits (12) which are individually analyzed is essentially equal to the number of subunits (12) in a complete dose of the multiple unit system.

5. The method according to claim 1, wherein said subunits (12) comprise at least one active drug.

6. The method according to any of the preceding claims, wherein said subunits (12) comprise a protective film.

7. The method according to claim 6, wherein the protective film is a film giving a controlled release of the active drug.

8. The method according to claim 6, wherein the protective film is an enteric coating polymer.

9. The method according to claim 1, wherein the step of individually analyzing said number of subunits (12) is performed by individually analyzing said subunits (12) in parallel.

10. The method according to claim 1, wherein the step of individually analyzing the subunits (12) comprises the step of performing a destructive test on the subunits (12).

11. The method according to claim 10, wherein said destructive test comprises a dissolution test, in which precise dissolution characteristics of each analyzed subunit (12) is individually monitored, and wherein dose-level dissolution characteristics of the multiple unit system are determined on the basis of the obtained dissolution characteristics of each analyzed subunit (12).

12. The method according to claim 11, wherein said dissolution test is monitored by a technique selected from the group consisting of absorption spectrometry, emission spectrometry, scattering spectrometry and electrochemical techniques.

13. The method according to claim 12, wherein said dissolution test is monitored by absorption spectrometry.

14. The method according to claim 13, wherein said dissolution test is performed with a spectrophotometer, comprising a microplate (14) having a plurality of wells (16), and wherein each subunit (12) to be individually analyzed is placed in a respective one of said wells (16).

15. The method according to claim 14, wherein the microplate (14) is tilted during the analysis in order to avoid interference from the subunits (12).

16. The method according to claim 14 or 15, wherein, in order to avoid interference from the subunits (12), the microplate (14) is shaken during the analysis in such a way that the subunits (12) present in each well (16) do not interfere with the optical path of the spectrophotometer.

17. The method according to claim 16, wherein, in order to avoid interference from the subunits (12), the contents of each well is subjected to stirring.

18. The method according to claim 17, wherein the stirring is achieved by a small glass bead in each one of the wells.

19. The method according to claim 1, wherein the step of individually analyzing the subunits (12) comprises the step of performing a non-destructive test on each analyzed subunit (12).

20. A process for the manufacture of multiple unit system formulations, comprising the method of claim 1, wherein the obtained precise characteristics for each individually analyzed subunit (12) are used as feed-back control data in the process in order to obtain predetermined dose-level characteristics of the manufactured multiple unit system formulations.

21. A process for designing a pharmaceutical unit dose of a multiple unit system comprising a plurality of individual subunits; the process comprising performing the method according to claim 1.

22. The method according to claim 13, wherein said absorption spectrometry is selected from the group consisting of UV-VIS, IR and NIR.

* * * * *

UNITED STATES PATENT AND TRADEMARK OFFICE
CERTIFICATE OF CORRECTION

PATENT NO : 6,162,465
DATED : December 19, 2000
INVENTOR(S) : Folestad, et al.

It is certified that error appears in the above-identified patent and that said Letters Patent is hereby corrected as shown below:

<u>ON THE TITLE PAGE</u>
Item [86] PCT No.: "PCT/SE96/01094 should read -- PCT/SE98/01094 --.

Signed and Sealed this

Twenty-ninth Day of May, 2001

Attest:

NICHOLAS P. GODICI

Attesting Officer         Acting Director of the United States Patent and Trademark Office